(12) United States Patent
Arzt et al.

(10) Patent No.: US 11,096,771 B2
(45) Date of Patent: Aug. 24, 2021

(54) DEVICE HAVING A STRUCTURED COATING FOR THE TREATMENT OF EARDRUM PERFORATIONS

(71) Applicant: Leibniz-Institut für Neue Materialien gemeinnützige GmbH, Saarbrücken (DE)

(72) Inventors: Eduard Arzt, Saarbrücken (DE); Sarah Fischer, Kleinblittersdorf (DE); Klaus Kruttwig, Saarbrücken (DE); René Hensel, Saarbrücken (DE); Bernhard Schick, Hofbieber (DE); Gentiana Wenzel, Homburg (DE)

(73) Assignee: Leibniz-Institut für Neue Materiallen gemeinnützige GmbH, Saarbrücken (DE)

( * ) Notice: Subject to any disclaimer, the term of this patent is extended or adjusted under 35 U.S.C. 154(b) by 54 days.

(21) Appl. No.: 16/317,048

(22) PCT Filed: Jul. 26, 2017

(86) PCT No.: PCT/EP2017/068872
§ 371 (c)(1),
(2) Date: Jan. 11, 2019

(87) PCT Pub. No.: WO2018/019879
PCT Pub. Date: Feb. 1, 2018

(65) Prior Publication Data
US 2019/0282353 A1    Sep. 19, 2019

(30) Foreign Application Priority Data

Jul. 28, 2016    (DE) .................... 10 2016 113 956.4

(51) Int. Cl.
*A61F 2/18*    (2006.01)
*A61F 2/00*    (2006.01)
(Continued)

(52) U.S. Cl.
CPC .............. *A61F 2/0077* (2013.01); *A61F 2/18* (2013.01); *A61L 27/3691* (2013.01);
(Continued)

(58) Field of Classification Search
CPC .... A61F 2/0077; A61F 2/18; A61F 2002/183; A61F 2210/0076; A61F 2240/001;
(Continued)

(56) References Cited

U.S. PATENT DOCUMENTS 5,376,117 A * 12/1994 Pinchuk ................ A61F 2/0077
623/8
8,192,668 B2    6/2012 Spatz et al.
(Continued)

FOREIGN PATENT DOCUMENTS

CN    103619282 A    3/2014
DE    102010026490 A1    1/2012
(Continued)

OTHER PUBLICATIONS https://www.engineeringtoolbox.com/young-modulus-d_417.html (Year: 2013).*
(Continued)

*Primary Examiner* — Brian A Dukert
*Assistant Examiner* — Rebecca Lynee Zimmerman
(74) *Attorney, Agent, or Firm* — Cahn & Samuels, LLP

(57) ABSTRACT

A device having a structured coating for adhering to rough, in particular biological, surfaces, includes a carrier layer, wherein a plurality of protrusions is arranged on the carrier layer, which protrusions each comprise at least a shaft having an end face pointing away from the surface, and wherein a further layer is arranged at least on the end face, wherein the layer has a different modulus of elasticity than the protrusion in question. The further layer can also fill the
(Continued)

intermediate spaces between the protrusions such that an internal structured coating is produced.

13 Claims, 17 Drawing Sheets

(51) Int. Cl.
    *A61L 27/36*     (2006.01)
    *A61L 27/50*     (2006.01)
    *A61B 17/00*     (2006.01)

(52) U.S. Cl.
    CPC ........... *A61L 27/50* (2013.01); *A61B 17/0057* (2013.01); *A61F 2002/183* (2013.01); *A61F 2210/0076* (2013.01); *A61F 2240/001* (2013.01); *A61L 2400/18* (2013.01); *A61L 2420/02* (2013.01); *A61L 2430/14* (2013.01)

(58) Field of Classification Search
    CPC ............... A61F 2002/0081; A61F 2/12; A61L 27/3691; A61L 27/50; A61L 2400/18; A61L 2420/02; A61L 2430/14; A61L 27/3895; A61B 17/0057; A61B 17/1615; B32B 3/30; A21B 3/138; Y10T 428/28; C09J 2301/31
    See application file for complete search history.

(56) References Cited

U.S. PATENT DOCUMENTS

| | | | |
|---|---|---|---|
| 8,636,797 | B2 | 1/2014 | Chitre et al. |
| 8,771,354 | B2 | 7/2014 | Picha et al. |
| 9,140,697 | B2 | 9/2015 | Tseng et al. |
| 9,624,101 | B2 | 4/2017 | Mardilovich et al. |
| 10,005,103 | B2 | 6/2018 | Artz et al. |
| 10,046,541 | B2 | 8/2018 | Schneider et al. |
| 2002/0182241 | A1* | 12/2002 | Borenstein ............... B29C 65/56 424/422 |
| 2004/0028875 | A1* | 2/2004 | Van Rijn ............... B01D 67/002 428/98 |
| 2006/0005362 | A1 | 1/2006 | Arzt et al. |
| 2006/0015053 | A1* | 1/2006 | Crisp ..................... A61N 1/205 602/43 |
| 2012/0100217 | A1* | 4/2012 | Green ..................... C08L 71/02 424/487 |
| 2013/0245758 | A1* | 9/2013 | Chitre ............... A61M 39/0208 623/8 |
| 2014/0329061 | A1 | 11/2014 | Lu et al. |
| 2017/0361508 | A1* | 12/2017 | Carter ..................... B29C 39/26 |
| 2018/0051187 | A1 | 2/2018 | Hensel et al. |
| 2018/0223886 | A1 | 8/2018 | Kroner et al. |

FOREIGN PATENT DOCUMENTS

| | | |
|---|---|---|
| DE | 102012112965 A1 | 6/2014 |
| DE | 102014119470 A1 | 6/2016 |
| WO | 2007096082 A1 | 8/2007 |
| WO | 2010108003 A2 | 9/2010 |
| WO | 2012054039 A1 | 4/2012 |
| WO | 2013063069 A1 | 5/2013 |
| WO | 2016146792 A1 | 9/2016 |
| WO | 2019129476 A1 | 7/2019 |
| WO | 2019129508 A1 | 7/2019 |
| WO | 2019129540 A1 | 7/2019 |
| WO | 2019185441 A1 | 10/2019 |

OTHER PUBLICATIONS https://web.archive.org/web/20201112021225/http://www.matweb.com/search/DataSheet.aspx?MatGUID=2fe782a31c4b4bed984b49651762b086&ckck=1 (Year: 2020).*
https://web.archive.org/web/20171217110707/http://www.matweb.com/search/DataSheet.aspx?MatGUID=Cbe7a469897a47eda563816c86a73520 (Year: 2017).*
Mata, A, Fleischman, A, Shuvo, R "Characterization of Polydimethylsiloxane (PDMS) Properties for Biomedical Micro/Nanosystems" Biomedical Microdevices 7:4, 281-293, 2005 (Year: 2005).*
English abstract of WO2007096082 A1, Aug. 30, 2017.
English abstract of WO2013063069 A1, May 2, 2013.
Mandavi et al, "A biodegradable and biocompatible gecko-inspired tissue adhesive", PNAS, vol. 105, No. 7, pp. 2307-12 (2008).
English abstract of DE102014119470 A1, Jun. 23, 2016.
English abstract of DE102012112965 A1, Jun. 26, 2014.
English abstract of WO2012054039 A1, Apr. 26, 2012.
English abstract of WO2010108003 A2, Sep. 23, 2010.
English abstract of DE102010026490 A1, Jan. 12, 2012.
Mota et al., "Multiscale fabrication of biomimetic scaffolds for tympanic membrane tissue engineering", Biofabrication, 2015, vol. 7, No. 2, 1-21.
English abstract of WO2016146792 A1, Sep. 22, 2016.
Translation of the International Preliminary Report on Patentability, dated Feb. 7, 2019.
English Abstract of WO 2019129508A1, Jul. 4, 2019.
English Abstract of WO 2019129476A1, Jul. 4, 2019.
English Abstract of WO 2019129540A1, Jul. 4, 2019.
English Abstract of WO 2019185441A1, Oct. 3, 2019.
English Abstract for CN103619282 A, Mar. 5, 2014.

* cited by examiner a)

b)

c)

A

B

DEVICE HAVING A STRUCTURED COATING FOR THE TREATMENT OF EARDRUM PERFORATIONS

This patent application is a U.S. national stage application of PCT international application PCT/EP2017/068872 filed on 26 Jul. 2017 and claims priority of German patent document 10 2016 113 956.4 filed on 28 Jul. 2016, the entireties of which are incorporated herein by reference.

FIELD OF THE INVENTION

The invention relates to a device having a structured coating, in particular for adhering to rough, in particular biological surfaces, such as for example eardrums.

BACKGROUND OF THE INVENTION

Adhesion to rough surfaces is often problematic. In the biological field in particular, many adhesives show only unsatisfactory properties. At the same time, it is problematic that the surface of the adhesives is only insufficiently compatible with biological processes such as wound healing.

An alternative is offered by dry adhesive substances, such as gecko structures, for example, which can also show adhesion to rough surfaces without the intermediary of adhesives. However, these substances must be produced quite frequently and are only adaptable to a limited extent.

Eardrum perforations are a frequently-occurring problem that can lead to hearing loss or frequently recurring infections. Common causes of eardrum perforations can be middle ear infections, trauma, and postoperative complications. As a rule, one can distinguish between acute (smaller) perforations, which spontaneously close in most cases, and larger or chronic perforations. These larger perforations must be surgically treated by myringoplasty or tympanoplasty, procedures that have a high success rate, but in addition to the surgical risk, there is also a risk of residual perforation. In tympanoplasty, moreover, autologous tissue is transplanted, which must be additionally removed. One of the main problems in the regeneration of eardrum injuries is the lack of a carrier layer for the migration of epithelial cells and the formation of a trilayer membrane. As "supporting platforms" one can generally use either transplanted tissue or polymers, the function of which can then be improved by using biomolecules. Polymers that can be used for this purpose include gelatin, silk fibroin, chitosan, alginates or poly(glycerol sebacates). A current survey of results in the use of these polymers and various growth factors can be found in the overview by Hong et al. Although many of the polymers used lead to outstanding results with respect to closure of the perforation, there are significant differences in the morphology of the tissue in question.

The object of the invention is to provide a device having a structured coating that shows adhesion in particular to rough surfaces, in particular biological surfaces, and avoids the drawbacks of prior art.

SUMMARY OF THE INVENTION

This object is achieved by the inventions having the features of the independent claims. Advantageous improvements of the inventions are described in the dependent claims. The wording of all of the claims is hereby included in the content of this description by reference. The inventions also comprise all reasonable combinations, and in particular all mentioned combinations of the independent and/or dependent claims.

The object is achieved by means of a device having a structured coating, wherein the device comprises a carrier layer, wherein a plurality of protrusions (pillars) is arranged on this carrier layer, which protrusions each comprise at least a shaft having an end face facing away from the surface, characterized in that a further layer is arranged at least on the end face, wherein this layer has a different elastic modulus from the protrusion in question.

This further layer also forms the top surface of the device, which is used for adhesion to a surface.

In a perpendicular direction, the device therefore comprises, at the position of a protrusion, at least two layers starting from the carrier layer differing in elastic modulus, specifically at least the protrusion and the further layer arranged thereon. This further layer and the end face of a protrusion form an interface between two areas differing in elastic modulus. Depending on the production method, the interfaces can also comprise thin layers of bonding auxiliaries.

The elastic modulus should preferably be constant within a particular area.

A protrusion itself can also have further areas differing in elastic modulus.

The further layer preferably has a lower elastic modulus than the protrusion on which it is arranged. By means of this structure, the shaft of the protrusion is less elastic than the further layer. The shaft of the pillar therefore shows less of a tendency toward agglomeration with or without loading. At the same time, the upper part of the protrusion is more elastic and can better adapt itself to rough and/or soft surfaces.

In a further embodiment of the invention, the interface between the further layer and the end face is not parallel to the surface of the further layer with respect to the respective protrusion.

In an embodiment of the invention, the end face of a protrusion is curved. Preferably, it comprises a peak within the protrusion. In particular, it has a parabolic or hemispherical shape. In this manner, the interface with the further layer also has a corresponding shape. Here, the end face can show a curvature only as far as the edge of the protrusion, while it has a flat course in the middle of the protrusion. In such an arrangement, the thickness of the further layer above the end face is not constant. If the end face forms a peak in the middle of the protrusion and the surface of the further layer has a flat shape, then the thickness of the further layer decreases above the protrusion toward the middle of the protrusion.

As a result of such a shape of the interface, materials having differing elasticity or bending stiffness are present and engage with one another. It has been found that such an arrangement increases the adhesive force of such a protrusion and also decreases its tendency to collapse.

In an embodiment of the invention, the ratio of the minimum perpendicular thickness of the further layer above the protrusion to the height of the protrusion is less than 3, preferably less than 1, in particular less than 0.5, and in particular less than 0.2. In this manner, changes in the thickness of the further layer, e.g. in the case of curved phase interfaces due to the geometry of the protrusions, have a particularly strong effect on adhesion. The optimum ratio can also depend on the ratio of the elastic moduli, as well as the geometry of the interface.

In an embodiment of the invention, the curvature of the end face is convex in the direction of the further layer, i.e. the phase interface has a peak. Preferably, the curvature is a spherical curvature, in particular with a radius of up to twice the diameter of the protrusion, in particular of at least the diameter of the protrusion.

In a further embodiment of the invention, on detachment from a surface, the protrusion begins to detach in the middle. The advantageous parameters for elastic modulus, size ratio and geometry of the interface, in particular a convex interface, can be determined by simulations and measurements.

In a preferred embodiment of the invention, the protrusions on the carrier layer are configured as pillars. This means that these are protrusions preferably configured perpendicularly to the carrier layer that have a shaft and an end face, wherein the shaft and the end face may have any desired section (for example circular, oval, rectangular, quadratic, diamond-shaped, hexagonal, pentagonal, etc.).

Preferably, the protrusions are configured such that the perpendicular projection of the end face onto the base surface of the protrusion forms an overlapping surface with the base surface, wherein the overlapping surface and the projection of the overlapping surface onto the end face form an element on the end face that lies completely inside the protrusion. In a preferred embodiment of the invention, the overlapping surface comprises at least 50% of the base surface, preferably at least 70% of the base surface, and particularly preferably, the overlapping surface comprises the entire base surface. The protrusions are therefore preferably not sloping, but they may be.

In a preferred embodiment, the end face is oriented parallel to the base surface and to the top surface. If the end faces are not oriented parallel to the top surface and therefore have different perpendicular heights, the average perpendicular height of the end faces is considered to be the perpendicular height of the protrusion.

In a preferred embodiment of the invention, the shaft of the protrusion has, with respect to its average diameter, an aspect ratio of height to diameter of 1 to 100, preferably 1 to 10, and particularly preferably 2 to 5.

In an embodiment, the aspect ratio is greater than 1, preferably at least 3, in particular at least 7, preferably 3 to 15, and particularly preferably 3 to 10.

In this case, the average diameter is understood to refer to the diameter of the circle that has the same area as the corresponding section of the protrusion, averaged over the entire height of the protrusion.

In a further embodiment of the invention, the ratio of the height of a protrusion to its diameter at a specified height over the entire height of the protrusion is always 1 to 100, preferably 1 to 10, and particularly preferably 2 to 5. In an embodiment, this aspect ratio is at least 3, in particular at least 7, preferably 3 to 15, particularly preferably 3 to 10. In this case, diameter is understood to refer to the diameter of a circle having the same area as the corresponding section of the protrusion at the specified height.

The protrusions can have widened end faces, so-called "mushroom" structures. It is also possible for the further layer to extend beyond the end face and thus form a "mushroom" structure.

In a preferred embodiment, the protrusions do not have widened end faces.

The surface of the further layer can itself be structured so as to increase its surface. In this case, the average perpendicular height of the further layer is taken as the perpendicular thickness of the further layer.

In a preferred embodiment, the perpendicular height of all of the protrusions is in a range of 1 μm to 10 mm, preferably 1 μm to 5 mm, in particular 1 μm to 2 mm, and preferably in a range of 10 μm to 2 mm.

In a preferred embodiment, the perpendicular thickness of the further layer above an end face is in a range of 1 μm to 1 mm, preferably 1 μm to 500 μm, in particular 1 μm to 300 μm, preferably in a range of 1 μm to 200 μm, in particular in a range of 10 μm to 200 μm, and most preferably 5 μm to 100 μm.

Preferably, the further layer, with respect to at least 50% of the projection of the base surface of a protrusion onto the surface of the further layer, has a perpendicular thickness in the above range or one of the preferred ranges.

The smallest thickness of the further layer above a protrusion is preferably always less than the maximum perpendicular height of the protrusion.

In a preferred embodiment, the perpendicular thickness of the carrier layer is in a range of 1 μm to 2 mm, preferably 1 μm to 500 μm, and in particular 1 μm to 300 μm.

In a preferred embodiment, the base surface, in terms of its area, corresponds to a circle with a diameter of between 0.1 μm and 5 mm, preferably 0.1 μm and 2 mm, particularly preferably between 1 μm and 500 μm, and particularly preferably between 1 μm and 100 μm. In an embodiment, the base surface is a circle with a diameter of between 0.3 μm and 2 mm, preferably 1 μm and 100 μm.

The average diameter of the shafts is preferably between 0.1 μm to 5 mm, preferably 0.1 μm and 2 mm, and particularly preferably between 1 μm and 100 μm. Preferably, the height and the average diameter are adapted according to the preferred aspect ratio.

In a preferred embodiment with widened end faces, the surface of the end face of a protrusion, or the surface of the further layer, is at least 1.01 times, preferably at least 1.5 times larger than the area of the base surface of a protrusion. For example, it can be larger by a factor of 1.01 to 20.

In a further embodiment, the widened end face is between 5% and 100% larger than the base surface, particularly preferably between 10% and 50% of the base surface.

In a preferred embodiment, the distance between two protrusions is less than 2 mm, in particular less than 1 mm, and most preferably less than 500 μm or less than 100 μm.

The protrusions are preferably regularly arranged at periodic intervals.

In a preferred embodiment of the invention, the protrusions have a height of 5 to 50 μm, and preferably up to 25 μm. The further layer has a perpendicular thickness above the end faces of 3 to 70 μm. The average distance between the pillar-shaped protrusions is between 5 and 50 μm. The thickness of the carrier layer is between 5 and 100 μm. Depending on the distance between the protrusions, the diameter is 5 to 40 μm. Preferably, the protrusions are hexagonally arranged. Particularly preferably, the density of the protrusions is 10,000 to 1,000,000 protrusions/cm$^2$.

The total thickness of the device, comprising the further layer, the protrusions, and the carrier layer, is preferably between 50 μm and 300 μm.

The elastic moduli of all areas of the protrusion and the further layer are preferably 50 kPa to 3 GPa. Preferably, the elastic modulus of soft areas, i.e. in particular the further layer, is 50 kPa to 20 MPa, preferably 100 kPa to 10 MPa. Independently of this, the elastic modulus of the areas with a high elastic modulus, e.g. the protrusions and e.g. the carrier layer, is preferably 1 MPa to 3 GPa, and more preferably 2 MPa to 1 GPa. Preferably, the elastic moduli of all softer and harder areas are in the ranges given above.

The ratio of the elastic moduli between the lowest elastic modulus and the area with the highest elastic modulus is preferably less than 1:2000, in particular less than 1:1500, preferably less than 1:1200, independently thereof at least 1:1.1, preferably at least 1:1.5, and in particular at least 1:2. In this case, a ratio of up to 1:1000 can be advantageous. Preferably, the further layer has the lowest elastic modulus. In particular, the ratio is 1:1.1 to 1:500, and preferably 1:2 to 1:500.

In a further embodiment of the invention, the ratio of the elastic moduli of the area of the device with the lowest elastic modulus and the area with the highest elastic modulus is preferably 1:2 to 1:200 (soft to hard), and in particular 1:2 to 1:100.

In a further embodiment, the ratios indicated above describe the ratio of the elastic modulus of the further layer (soft) to that of the protrusions (hard).

In a particularly preferred embodiment of the invention, the further layer additionally fills the intermediate spaces between the protrusions.

In this embodiment, the device can be seen as a coating composed of at least two components, wherein these two components have a structured interface between them because of the protrusions now embedded in the coating. The upper side of the further layer preferably has a planar shape, and the underside of the carrier layer also preferably has such a shape. The indications given on the thickness of the further layer refer to the part of the further layer arranged above the end faces.

The protrusions are additionally stabilized by filling of the intermediate spaces. It was surprisingly found that such layers also show increased adhesion. The enclosed protrusions are also stabilized by the material surrounding them. Because of this, tensile forces parallel to the contact surface of the device do not cause collapsing of the protrusions, but the adhesive force remains present even in the event of such tensile forces. This is important for example if, in addition to adhesion, the device is also intended to withstand tensile forces parallel to the contact surface. An example of this is application on wounds to be closed or injuries of the eardrums.

Moreover, this layer can easily be kept clean or sterile, as no contamination whatsoever can accumulate in the intermediate spaces.

Additionally, the filled structure makes it possible to reduce stress peaks that may occur in the case of freestanding protrusions on detachment from a surface.

In addition, such a device can more easily be produced, as one need simply coat the carrying layer having the protrusions with the material of the further layer. Complex structuring steps are not required.

The surface of the device in this embodiment appears closed and uniform. This allows it to be more easily modified for adaptation to particular applications. In this case, treatment of the surface does not affect structuring inside the coating.

The surface can thus be functionalized or treated using known methods.

In a further embodiment of the invention, the further layer part is a film that connects the protrusions. In this case, the intermediate spaces between the protrusions are not filled.

The film preferably has a thickness that is less than 100%, preferably less than 50%, and particularly preferably less than 30% of the perpendicular height of the bridged protrusions. In this case, the film is not included in calculation of the height.

The film preferably has a thickness of less than 2 mm, preferably less than 1 mm, and particularly preferably less than 800 µm.

The protrusions may be composed of many different materials, and are preferably elastomers, particularly preferably crosslinkable elastomers. The areas with a higher elastic modulus can also comprise duroplasts.

The protrusions and the further layer can therefore comprise the following materials:

Epoxy- and/or silicone-based elastomers, polyurethanes, epoxy resins, acrylate systems, methacrylate systems, polyacrylates as homo- and copolymers, polymethacrylates as homo- and copolymers (PMMA, AMMA acrylonitrile/methyl methacrylate), polyurethane(meth)acrylates, silicones, silicone resins, rubbers such as R rubber (NR natural rubber, IR polyisoprene rubber, BR butadiene rubber, SBR styrene-butadiene rubber, CR chloropropene rubber, NBR nitrile rubber, M rubber (EPM ethene-propene rubber, EPDM ethylene-propylene rubber), unsaturated polyester resins, formaldehyde resins, vinyl ester resins, polyethylenes as homo- or copolymers, and mixtures and copolymers of the above-mentioned materials. Also preferred are elastomers approved for use in the field of packaging, medicinal products and food products by the EU (according to EU Regulation No. 10/2011 of 14 Jan. 2011 published on 15 Jan. 2011) or the FDA or silicone-free UV curable resins from PVD and CVD process engineering. In this case, polyurethane(meth)acrylates stands for polyurethane methacrylates, polyurethane acrylates, and mixtures and/or copolymers thereof.

Hydrogels, for example based on polyurethanes, polyvinylpyrrolidone, polyethylene oxide, poly(2-acrylamido-2-methyl-1-propanesulfonic acid), silicones, polyacrylamides, hydroxylated polymethacrylates or starches can also be used.

Epoxy- and/or silicone-based elastomers, polyurethane (meth)acrylates, polyurethanes, silicones, silicone resins (such as UV-curable PDMS), polyurethane(meth)acrylates, and rubber (such as EPM, EPDM) are preferred.

Particularly preferred are crosslinkable silicones, such as for example polymers based on vinyl-terminated silicones.

Among the above-mentioned substances, for the further layer that is in contact with the surface, the epoxy- and/or silicone-based elastomers, polyurethane(meth)acrylates, polyurethanes, silicones, silicone resins (such as UV-curable PDMS), polyurethane(meth)acrylates, and rubber (such as EPM, EPDM), in particular crosslinkable silicones, such as for example polymers based on vinyl-terminated silicones, are particularly preferred.

The above-mentioned hydrogels or pressure-sensitive adhesives can also be used for the further layer.

In a further embodiment, the surface of the further layer is treated. This allows the properties of the surface to be influenced. This can take place by means of physical treatment such as plasma treatment, preferably with $Ar/O_2$ plasma.

Covalent or non-covalent bonds to additives on the surface can also be formed, for example in order to achieve a certain compatibility with the cells. Preferred are additives for supporting cell adhesion, such as e.g. poly-L-lysine, poly-L-ornithine, collagen, or fibronectin. Such additives are known from the field of cell culturing.

In application in the medical field in particular, it can be advantageous to store substances in one part of the device which are then slowly released. For example, these can be drugs such as antibiotics, or adjuvants for supporting cell adhesion or cell growth.

In a further embodiment, the protrusions and the carrier layer are configured as a single piece and are composed of the same material.

In a further embodiment, the device also comprises further layers, which can optionally be detachable. In this manner, the surfaces can be protected prior to use by detachable films. Further stabilizing layers can also be arranged on the carrier layer.

The carrier layer preferably has a thickness that is less than the maximum height of the protrusions arranged on it.

As the carrier layer, if it is composed of the same material as the protrusions, comprises a material having a higher elastic modulus, the thickness of the carrier layer can also be used to influence the elasticity of the entire device.

The device according to the invention is preferably configured for adhering to soft substrates.

The device according to the invention is configured in particular for adhering to biological tissues. For this purpose, it can be configured for example as a film. It can also be configured in combination with the devices to be secured in place. For example, these can be dressing material, but also electrodes or other medical devices such as implants, in particular implants that are not to be anchored on bones, or soft implants. For example, these can be iris implants. The invention therefore also relates to an implant comprising a device according to the invention, for example on at least a portion of the surface of the implant.

The invention further relates to use of an above-mentioned device for adhering to biological tissues. These can be any desired tissues, such as skin, but also internal tissues such as organ surfaces, wound surfaces, or eardrums. The device allows the combination of a well-tolerated surface with simultaneous adhesion to the biological tissue. The device therefore also serves as a growth substrate for the cell cultivation or for the new tissue to be formed.

Treatment of Eardrum Perforations

Because of its adhesion, the device adheres quite favorably to the surface of the eardrum, and even makes it possible to apply it under stress. Because of its structure, it adheres to the surrounding tissues and not only to the eardrum. Optionally, the device configured in this manner can comprise different areas having different adhesion. This can take place via the material or the layer thickness of the further layer, but also simply by distribution of the protrusions within the device.

The device, which is advantageously configured as a film, therefore comprises at least the carrier layer with the protrusions, and the further layer is applied to these protrusions in such a way that the intermediate spaces are filled. By means of the embodiment as a film, the device can easily be cut to the desired size. This can even be done personally by the person carrying out treatment, e.g. the physician.

Because of its structuring, the device adheres favorably to the tissue to which it is applied. In addition to the eardrum, this can also be the surrounding tissue. No liquid component, which could flow into the ear, is required for application of the device.

Depending on the material used, the device can also be transparent, such that the status of the tissue under the device can be observed, for example in order to confirm healing, without detaching the device. The device is preferably transparent.

Because of its dry adhesiveness, the device can easily be re-detached.

Surprisingly, it was also found that the devices according to the invention, in particular the device in which the further layer fills the intermediate spaces, show advantageous properties for cell cultivation, i.e. the cultivation of cells outside of an organism. The device can easily be cut to size. Because of the E modulus of the two layers, in particular of the further layer, on which the cells are cultivated, the device can be adapted to the cells to be cultivated (E modulus (brain cells): approx. 0.1-1 kPa; E modulus (muscle cells): approx. 8-17 kPa; E modulus (bone cells): approx. 25-40 kPa).

In particular, the device can be easily divided after cultivation of the cells so that various tests can be conducted based on the same cell culture. As the device can be transparent, the cultures obtained in this manner are also suitable for microscopic tests. For example, they can be cut using razor blades or a scalpel. The device can also be applied to common glass supports, e.g. round glass slides.

Alternatively, the device can also be used directly for cultivation in corresponding cultivation receptacles.

The surface of the device can also be physically or chemically treated for cultivation. This can be done for example by autoclaving, for example by steam sterilization at 50 to 200° C., in particular 100 to 150° C., at a pressure of 1 to 5 bar for 5 min to 3 h. In such autoclaving (121° C., 2 bar, 20 min), no significant change in adhesive stress was observed.

For example, the surface can be treated with poly-L-lysine, poly-L-ornithine, collagen, fibronectin, gelatin, laminins, keratin, tenascin or perlecan. Such additives are known from the field of cell culturing.

The invention also relates to a method for producing an embodiment of the device according to the invention.

Individual method steps will be described in further detail in the following. The steps do not necessarily have to be carried out in the order indicated, and the method to be described can also have further steps not mentioned here.

For this purpose, in a first step, a template is provided for molding the plurality of protrusions.

The material for the protrusions is introduced into this template, preferably as a liquid. Optionally, the material can also already be at least partially cured.

After this, the material for the carrier layer, i.e. the surface on which the protrusions are arranged, is applied to the template and cured. Particularly preferably, this is the same material as for the shafts of the protrusions, so that the carrier layer and the shafts can also be produced in one step, for example by directly introducing a larger amount of material.

In a next step, the carrier layer and the protrusions are detached from the template.

After this, the material for the further layer is applied to the surface with the protrusions in an amount such that the protrusions are completely covered. This can be carried out for example by doctoring or spin coating.

In a next step, the further layer is cured.

Further details and features will be found in the following description of preferred examples in connection with the dependent claims. In this case, the respective features can be implemented individually or as multiple features in combination with one another. The possibilities for achieving the object are not limited to the examples. For example, in all cases, ranges given include-unspecified-intermediate values and all conceivable partial intervals.

BRIEF DESCRIPTION OF THE DRAWINGS

The examples are shown schematically in the figures. The same reference numbers in the individual figures denote the elements that are identical, functionally identical, or correspond to one another with respect to their functions. More specifically, the figures show the following.

DETAILED DESCRIPTION OF INVENTION

Soft Skin Adhesive (SSA) from Dow Corning was used for the tests. These are vinyl-terminated silicones. By mixing two solutions, A and B, curing of the polymers is catalyzed and Pt is initiated. The tests were carried out with MG 7-9800. The compositions used are indicated in SSA A:B.

Figure 1:
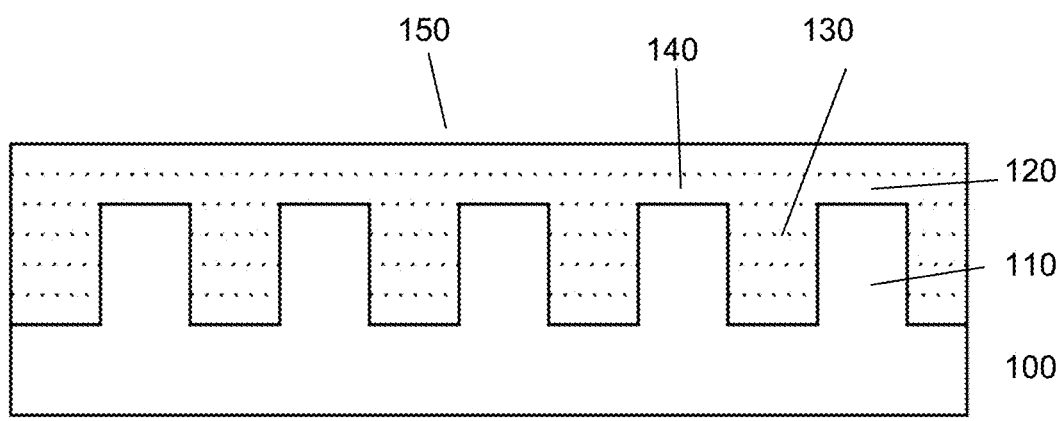
FIG. 1 A schematic view of a section of an embodiment of the invention.

FIG. 1 shows a schematic view of a section of an embodiment of the invention. The device comprises a carrier layer (100) on which a plurality of protrusions (110) is arranged. A further layer (120) is arranged on the end face (140) of the respective protrusions. In this case, this layer also fills the intermediate spaces (130) between the protrusions. The surface (150) of the further layer is the surface used for adhesion. The protrusions themselves preferably have a circular section and therefore constitute pillars.

Figure 2:
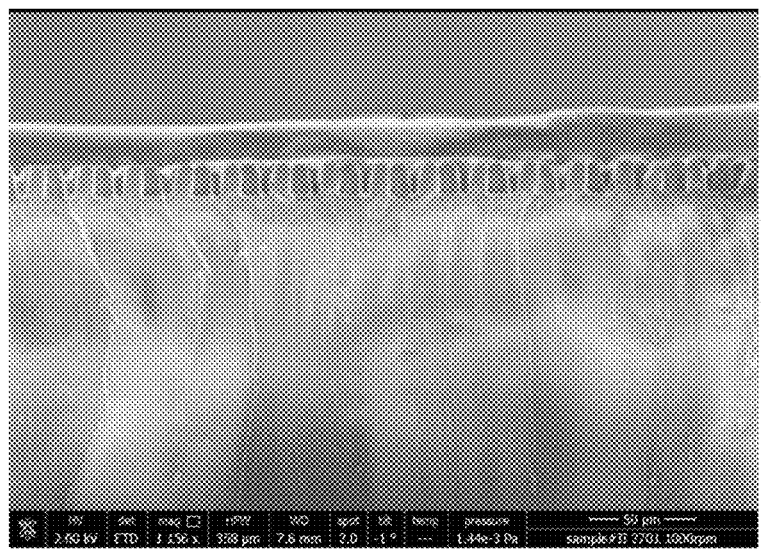
FIG. 2 SEM images of layers according to the invention; produced by spin coating of SSA 50:50 on a microstructured PDMS layer at 6000 rpm; the PDMS layer was produced with weights (100 g)
Figure 2:
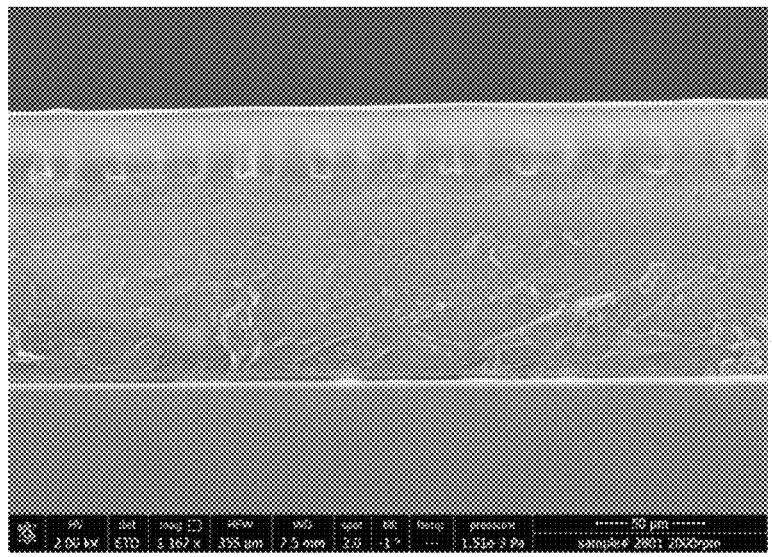
Figure 2:
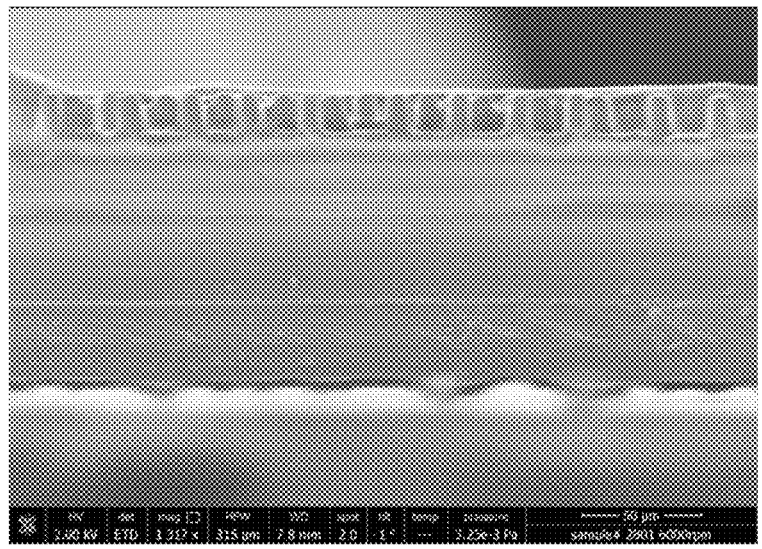

FIG. 2 shows SEM images (SEM: scanning electron microscope) that show the effect of increasing centrifugal acceleration in the production of the SSA layer on a microstructured PDMS surface.

The decrease in layer thickness with increasing revolution speed can be clearly seen.

Figure 3:
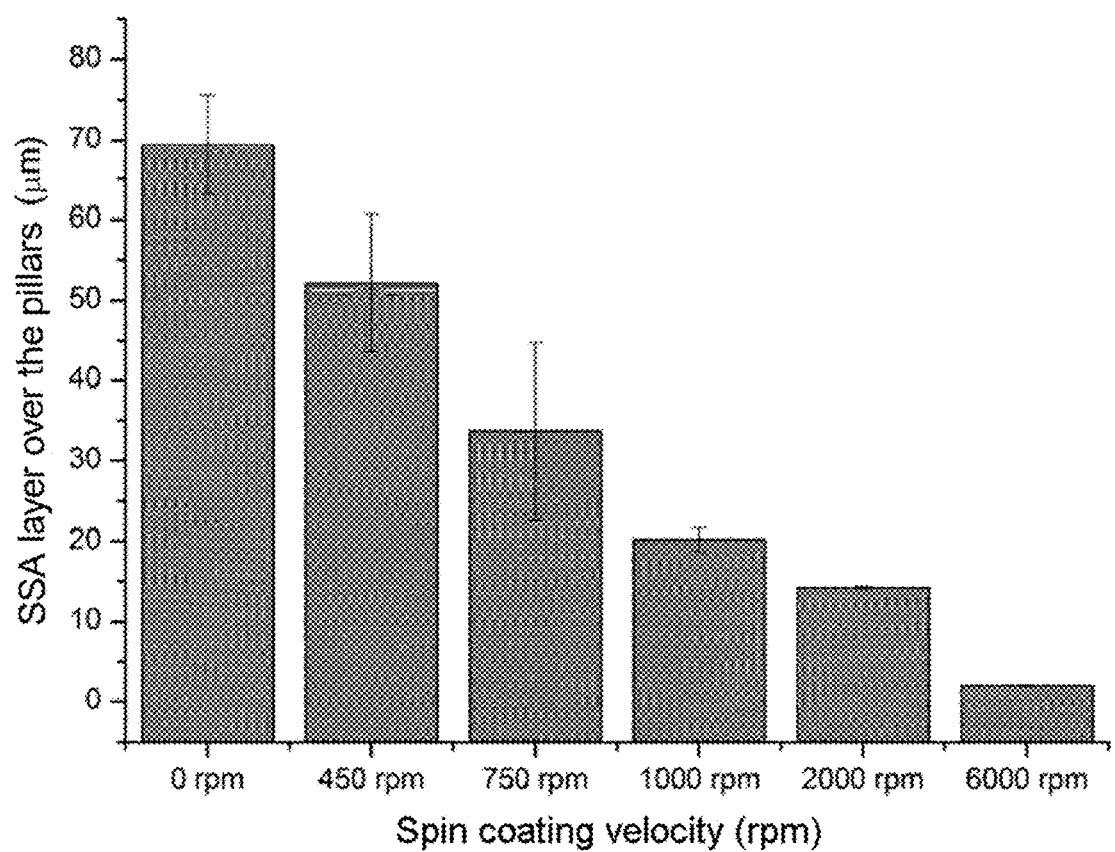
FIG. 3 Dependency of the layer thickness over the microstructured PDMS layer on spin coating velocity; all PDMS layers were produced with weights (100 g)

FIG. 3 shows the layer thicknesses as determined by SEM at different velocities (for 90 s respectively). In this case, the layer thickness is taken to be the thickness of the layer over the microstructured PDMS surface.

Figure 4:
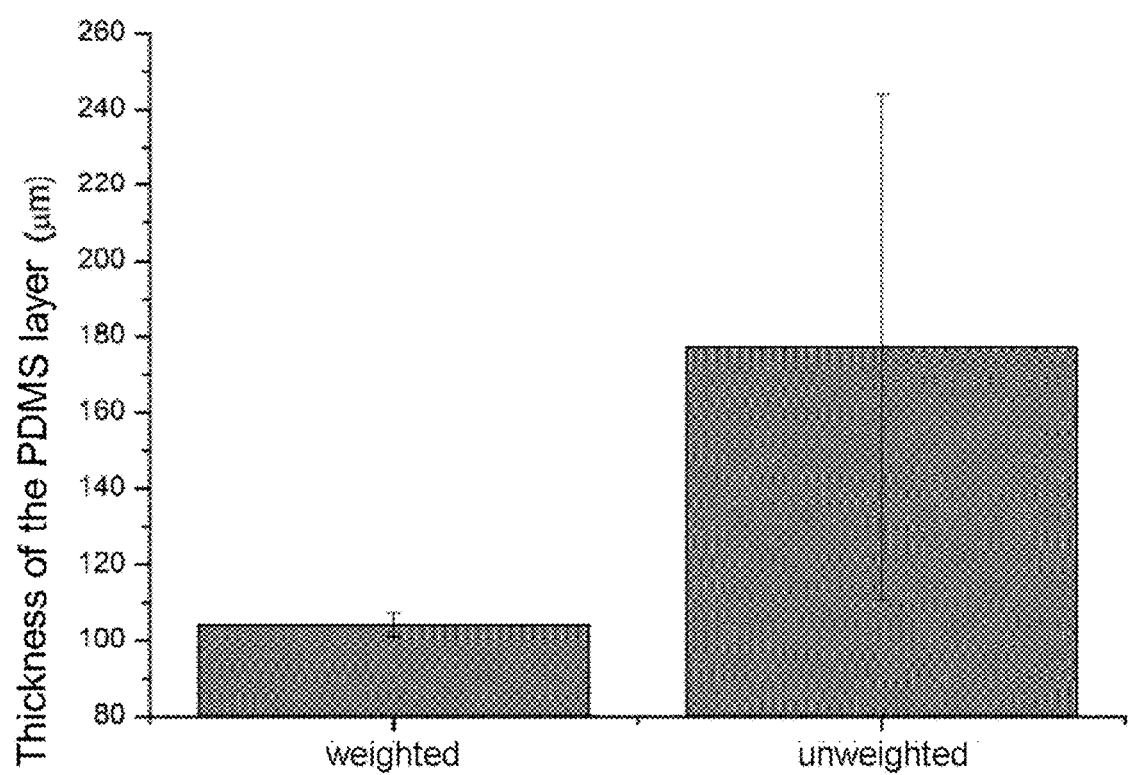
FIG. 4 A statistical evaluation of the obtained layer thickness depending on the use of weights.
Figure 19:
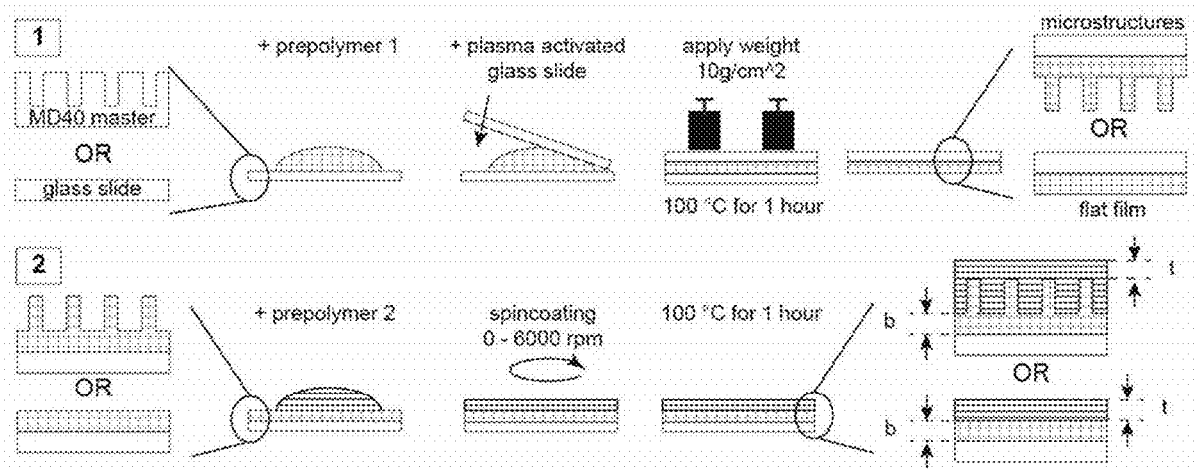
FIG. 19 Schematic view of the production process.

FIG. 4 shows the effect of weights on the layer thickness of the produced PDMS carrier layer (also see FIG. 19, upper method). By placing weights on the layer, thinner layers can be obtained. This allows more flexible devices to be obtained.

Figure 5:
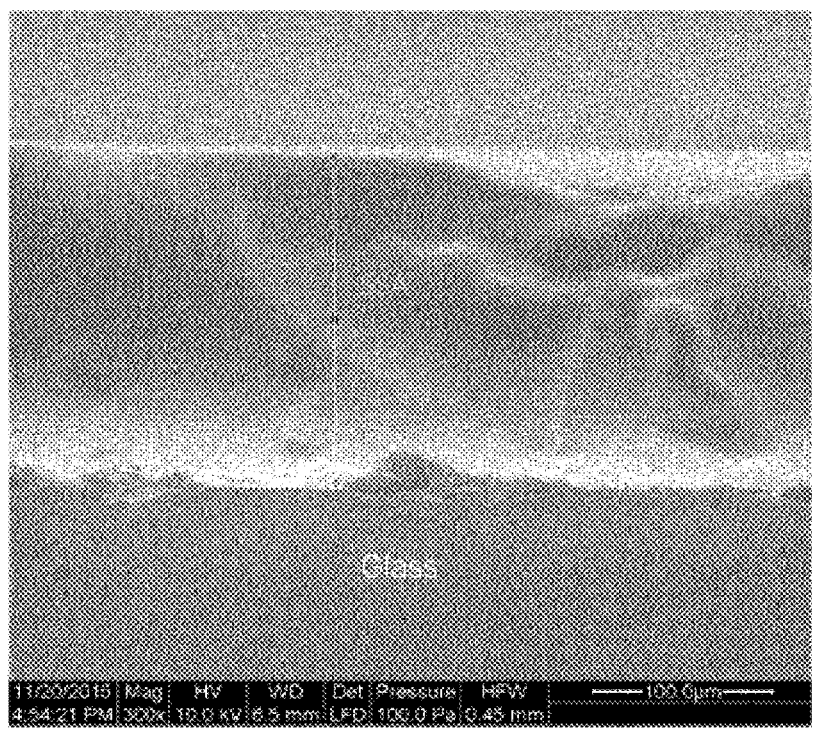
FIG. 5 An SEM image of a section through a layer of SSA 50:50 applied by spin coating to a glass substrate.
Figure 6:
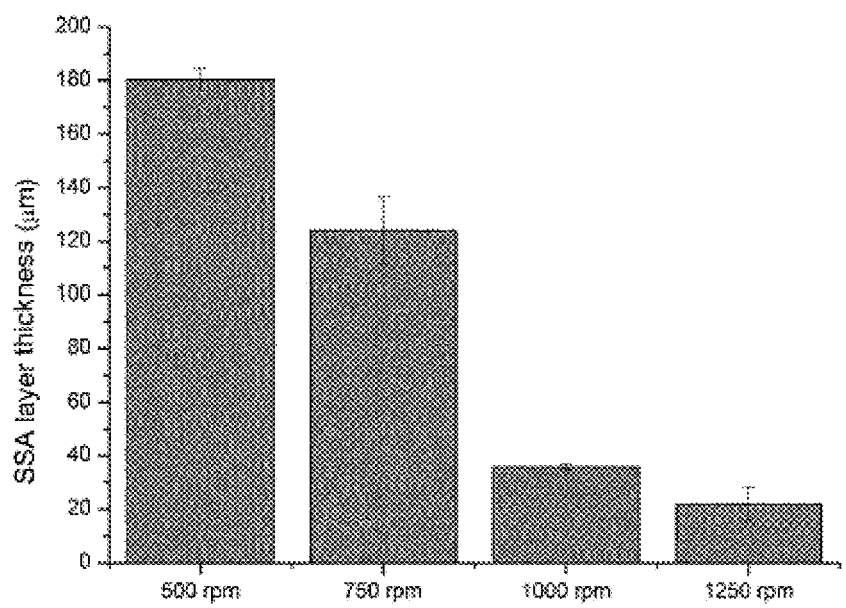
FIG. 6 Dependency of the layer thickness of SSA 50:50 on a glass surface on spin coating velocity.

FIG. 5 shows an SEM image of an SSA 50:50 layer on glass. In this case as well, the layer thickness can be set via the conditions during spin coating. The corresponding layer thicknesses obtained are shown in FIG. 6. The time was 90 s in all cases. However, similar layers can also be obtained at lower velocity and with a longer duration.

Figure 7:
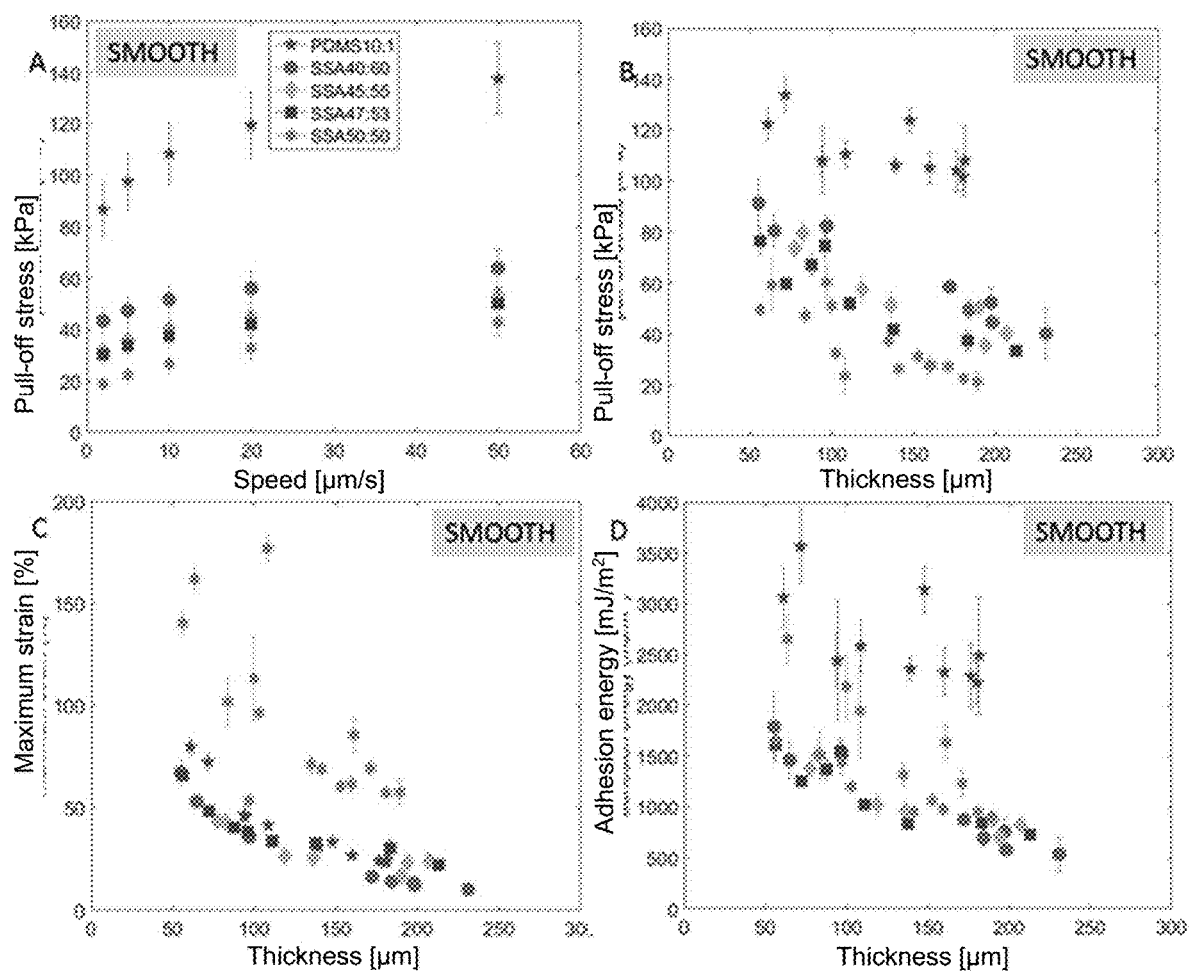
FIG. 7 Adhesion force of SSA and PDMS in various ratios against a smooth substrate (SMOOTH) in various applications; (A: pull-off stress vs. velocity; B: pull-off stress vs. layer thickness; C: maximum strain vs. layer thickness; D: adhesion energy vs. layer thickness; layer thickness was determined by SEM.
Figure 18:
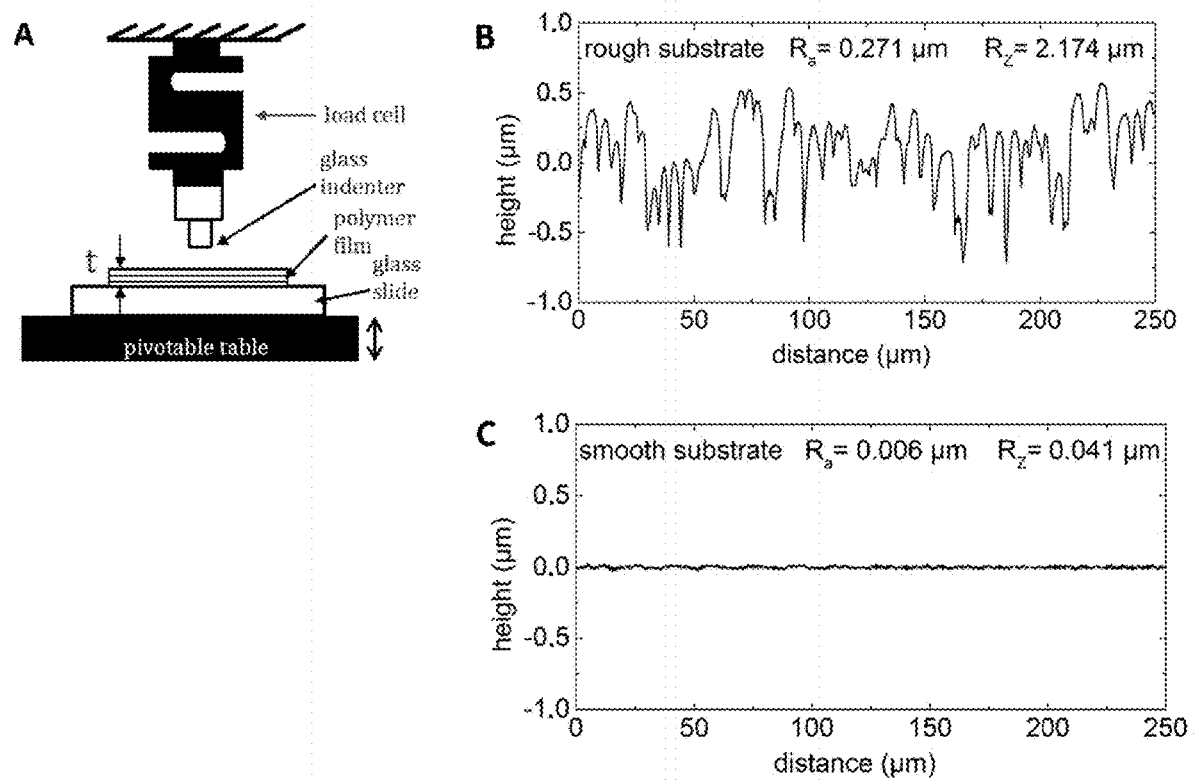
FIG. 18 Schematic structure of the measuring apparatus used to determine adhesion values (A). Determination of the roughness of the glass substrate used for the measurements. The curve (distance vs. height) for the smooth substrate shows virtually no deviations in contrast to the rough substrate.

FIG. 7 shows the values for measurement according to FIG. 18 in various applied layers. PDMS (Slygard 184) was used. The ratio indicates the proportions of PDMS and the crosslinker.

Various layer thicknesses (50 µm to 250 µm) were applied to a glass surface by means of the doctoring method. Increasing adhesion was measured with decreasing layer thickness. It can be seen for all of the materials that an increase in pull-off speed leads to higher adhesive stresses (FIG. A). There is a pronounced dependency between film thickness and all of the tested parameters for all of the SSA mixtures. These parameters include pull-off stress (FIG. B), maximum strain (FIG. C), and adhesion energy (FIG. D). Because of the considerably greater E modulus of PDMS, there is substantially less dependency of pull-off stress on film thickness in this case. It can be seen from FIG. B in particular that the pull-off stress depends on the E modulus of the materials. The stiffer the material, the higher the stresses observed. One notes on observation of maximum strain (FIG. C) that the maximum strain of SSA 50:50 is significantly greater than that of all the other materials tested.

Figure 8:
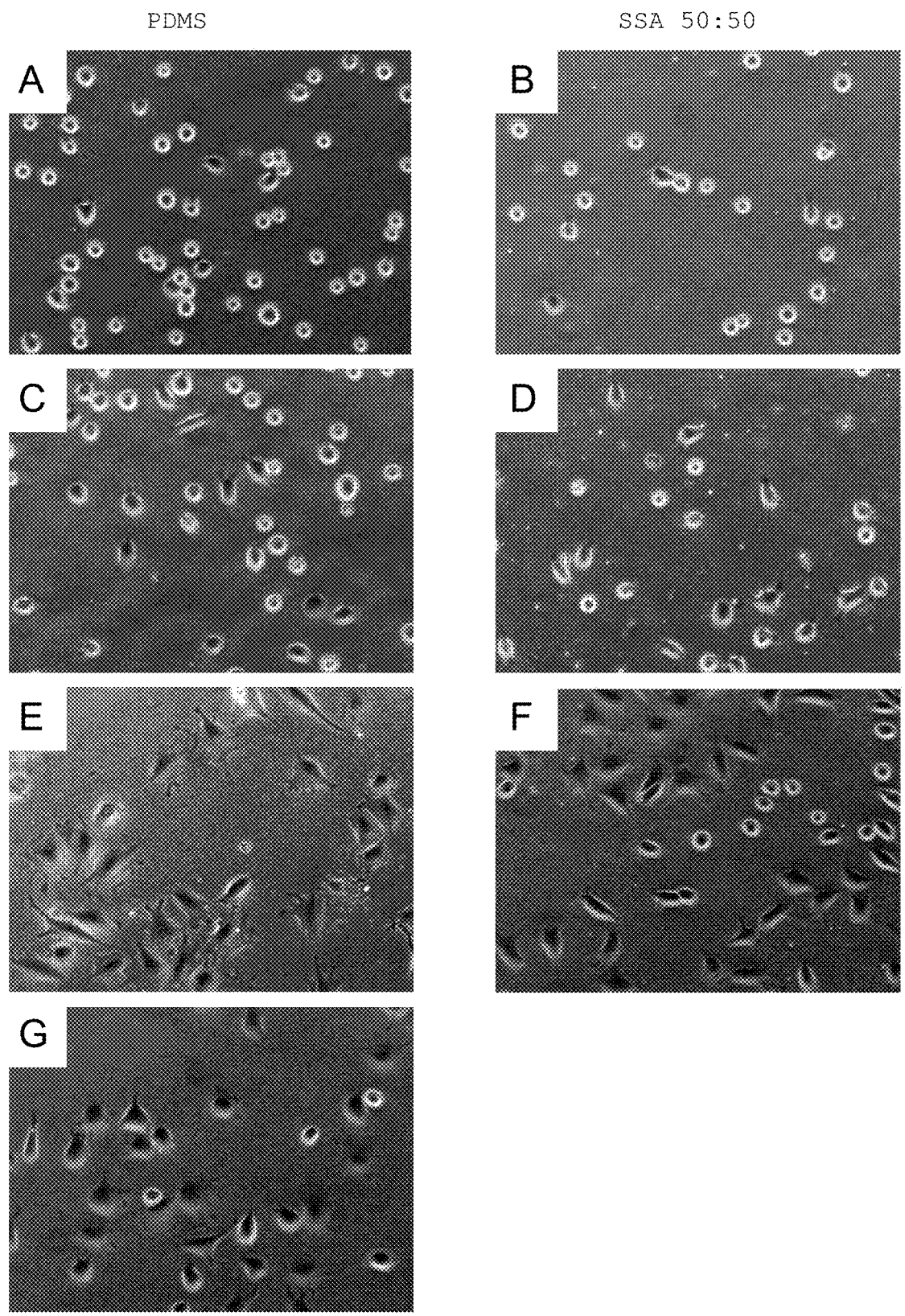
FIG. 8 Micrographs of L929 cells 4 h after plating on PDMS (A, C, E, G) or SSA 50:50 (B, D, F); unmodified (A and B); modified with poly-L-lysine (C and D); poly-L-ornithine and subsequent incubation with fibronectin (E and F); G cells cultivated on tissue-culture-treated (TC-treated) polystyrene.

FIG. 8 shows the effect of surface modification on the adhesion of L929 cells (fibroblasts, species mice). For this purpose, such cells were microscopically examined on the respective surfaces after a plating time of 4 h. For PDMS and SSA 50:50, minimal cell adhesion is seen when the surfaces are not modified (A and B). Adsorption of poly-L-lysine to the surface resulted in a clear increase in the adhesion behavior and the formation of cellular extensions for PDMS (C) and SSA 50:50 (D).

It was possible to significantly improve this adhesion behavior by treatment of the polymer surface with poly-L-ornithine and subsequent incubation with fibronectin for PDMS (E) and SSA 50:50 (F). In this case, the flattened cellular morphology is comparable to that of cell-culture-treated polystyrene. The adhesion properties of the SSA 50:50 were retained even after the surface modification.

Poly-L-ornithine and poly-L-lysine solutions were incubated for 20 min at 37° C. on the polymer surface; they were then rinsed with phosphate buffer (PBS). Bovine fibronectin was incubated for 60 min at 37° C. The concentration was 10 μg/ml PBS. After this, PBS washing and air-drying were carried out.

Figure 9:
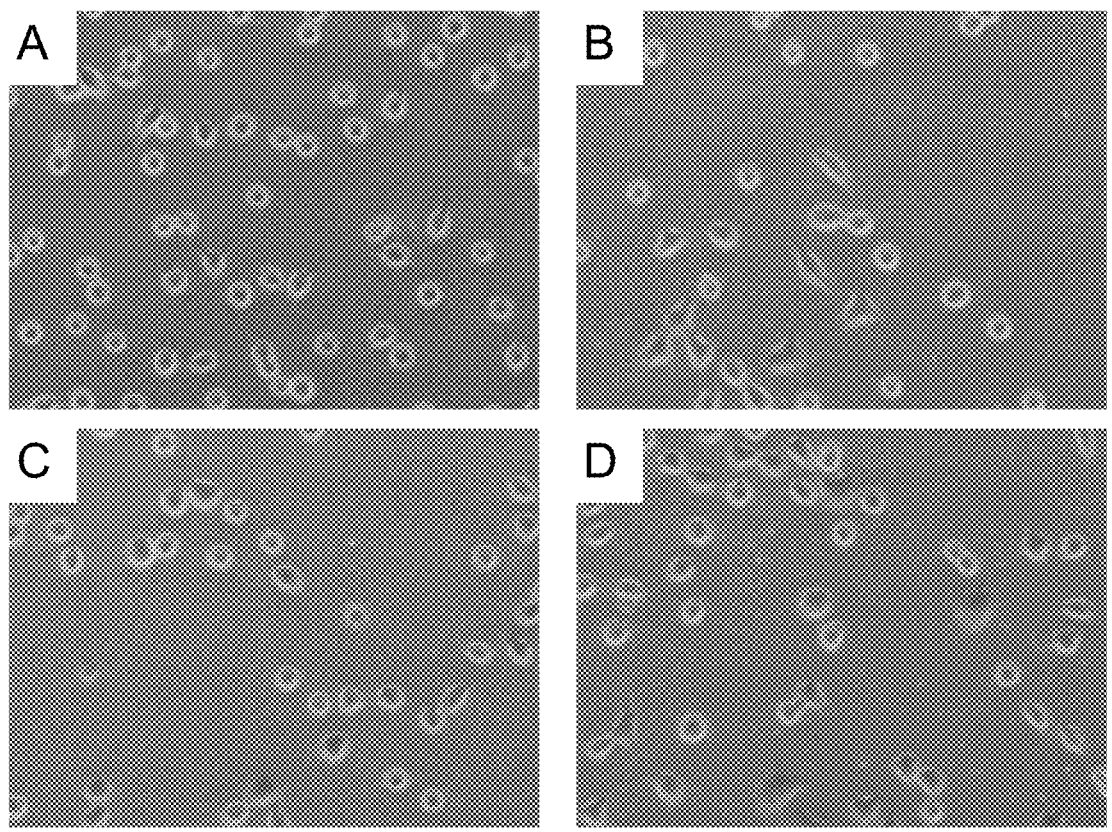
FIG. 9 Micrographs of L929 cells after 24 h on PDMS (A), SSA 50:50 (B), and treated respectively with $O_2$/Ar plasma-treated PDMS (C) or SSA 50:50 (D)
Figure 10:
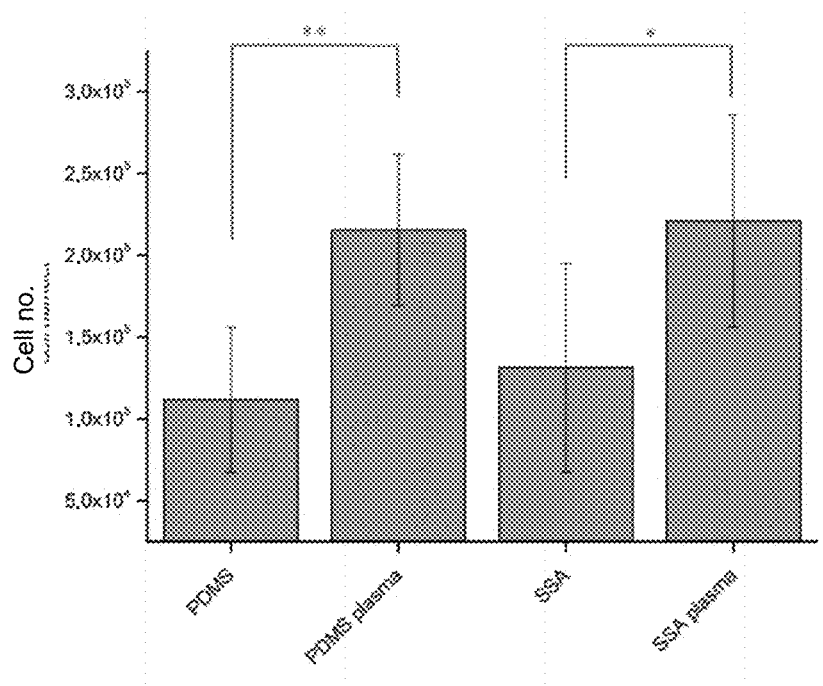
FIG. 10 Cell number after 24 h on the surfaces according to FIG. 9 starting from $3 \times 10^3$ vital cells (student's t test, * $p<0.05$ ** $p<0.0005$)
Figure 11:
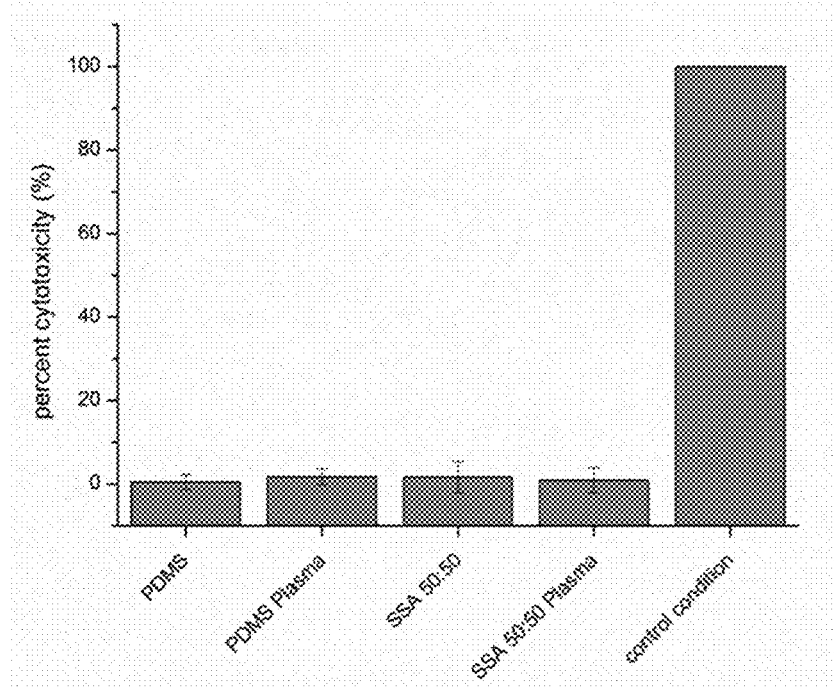
FIG. 11 Activity (in percent of cytotoxicity) of lactate dehydrogenase (LDH) after 24 h cultivation on the surfaces according to FIG. 9 and a control.
Figure 15:
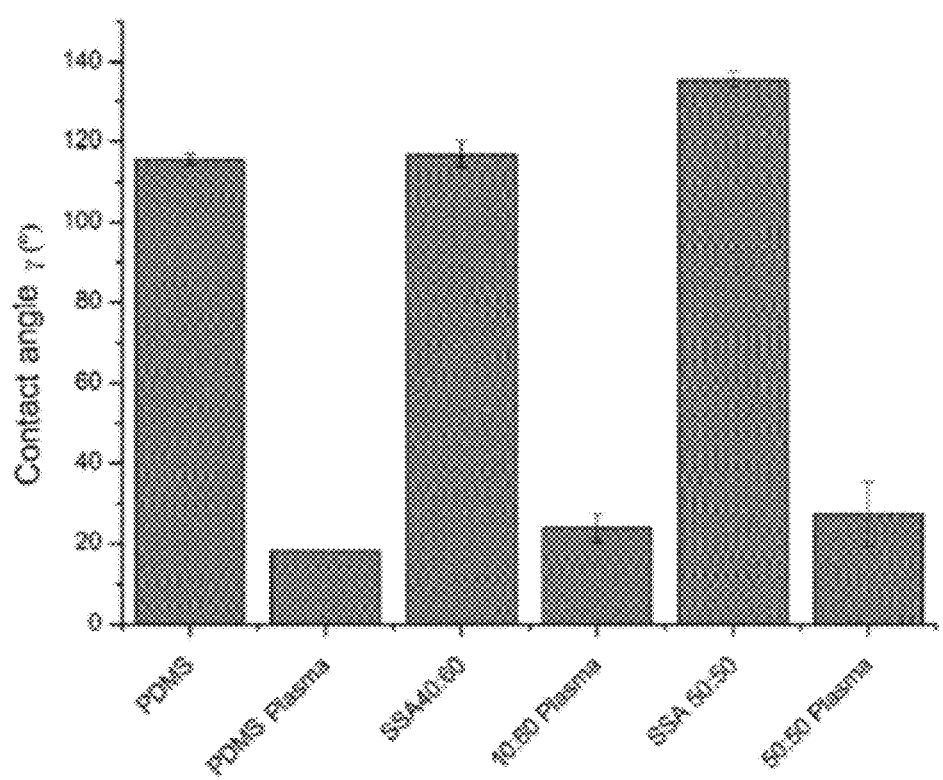
FIG. 15 Contact angle for various surfaces before and after plasma treatment (left to right: PDMS; PDMS plasma; SSA 40:60; SSA 40:60 plasma; SSA 50:50; SSA 50:50 plasma)

The adhesion behavior of L929 cells on PDMS and SSA 50:50 after a cultivation time of 24 h was also investigated. For this purpose, $3 \times 10^3$ vital cells were cultivated for 24 h on PDMS (A), SSA 50:50 (B), plasma-treated PDMS (C), and SSA 50:50 (D) (FIG. 9). After this period of time, the cells were enzymatically removed from the surface and the cell number was determined (FIG. 10). In order to test for a cytotoxic effect of cultivation on PDMS or SSA 50:50, lactate dehydrogenase (LDH) activity after 24 h of cultivation was investigated (FIG. 11). No cytotoxic effect was observed under any of the conditions. The effect of plasma treatment on the contact angle of the surface is shown in FIG. 15.

Figure 12:
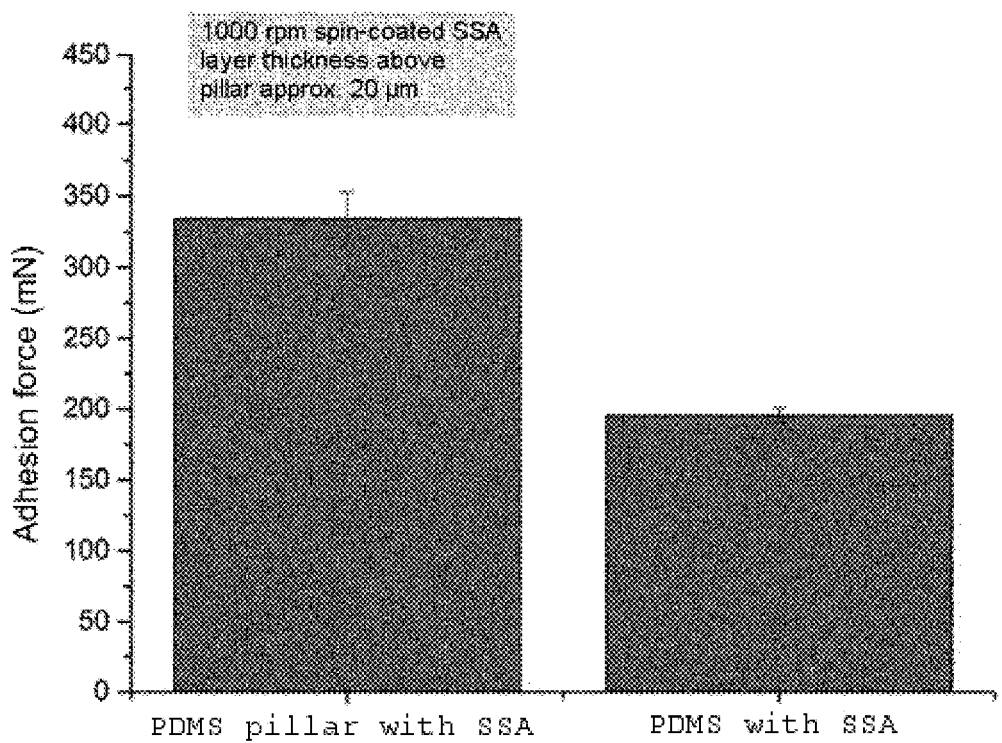
FIG. 12 Comparison of the adhesion force of structured coatings (PDMS/SSA 50:50; 20 µm layer thickness SSA 50:50 over the protrusions) and unstructured coating PDMS/SSA 50:50.

FIG. 12 shows the effect of structuring. Microstructured surfaces that were coated with SSA 50:50 affect the adhesion force. SSA 50:50 was applied by spin-coating to a microstructured PDMS layer with pillar heights of 20 μm. The adhesion force of the coated pillar structures is significantly higher in areas in which no protrusions are present. The measurement was carried out on the same sample, which had structured and unstructured areas.

Figure 13:
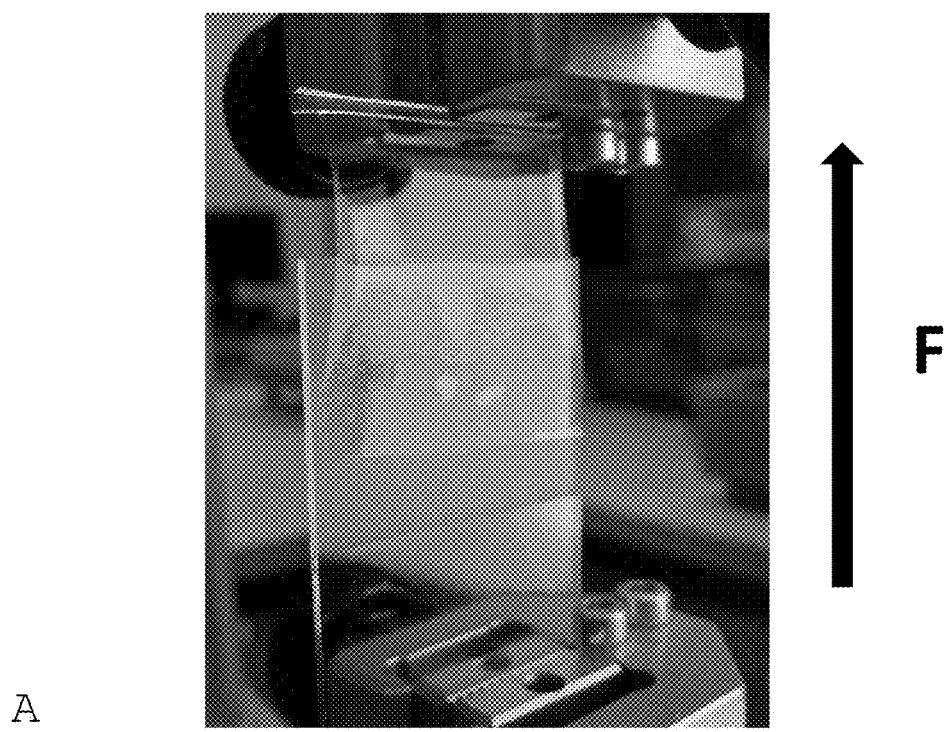
FIG. 13 Tensile force tests with unstructured coatings of Vitro-Skin® (structure shown in A); B shows the measured tensile forces for PDMS (reference) and PDMS, to which SSA was applied in various mixing ratios from 40:60 to 52:48.
Figure 13:
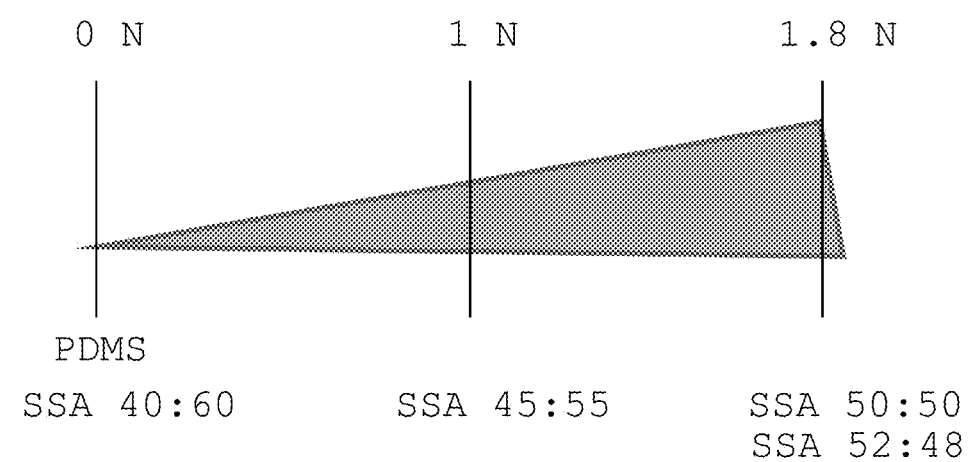

FIG. 13 shows the structure for tensile force tests with unstructured two-layer composites against Vitro-Skin®. For this purpose, a two-layer composite composed of a PDMS layer to which the SSA was applied in mixing ratios of 40:60 to 52:48 was produced. A preparation composed of PDMS was used as a reference. FIG. 13 A shows an example of the structure of the test. Vitro-Skin® is a synthetic material that simulates the surface properties of human skin (roughness $R_a$=12-15 μm). PDMS and SSA in a mixing ratio of 40:60 showed no adhesion whatsoever. Maximum adhesion was obtained with SSA in the mixing ratios of 50:50 and 52:48 (FIG. 13 B).

Figure 14:
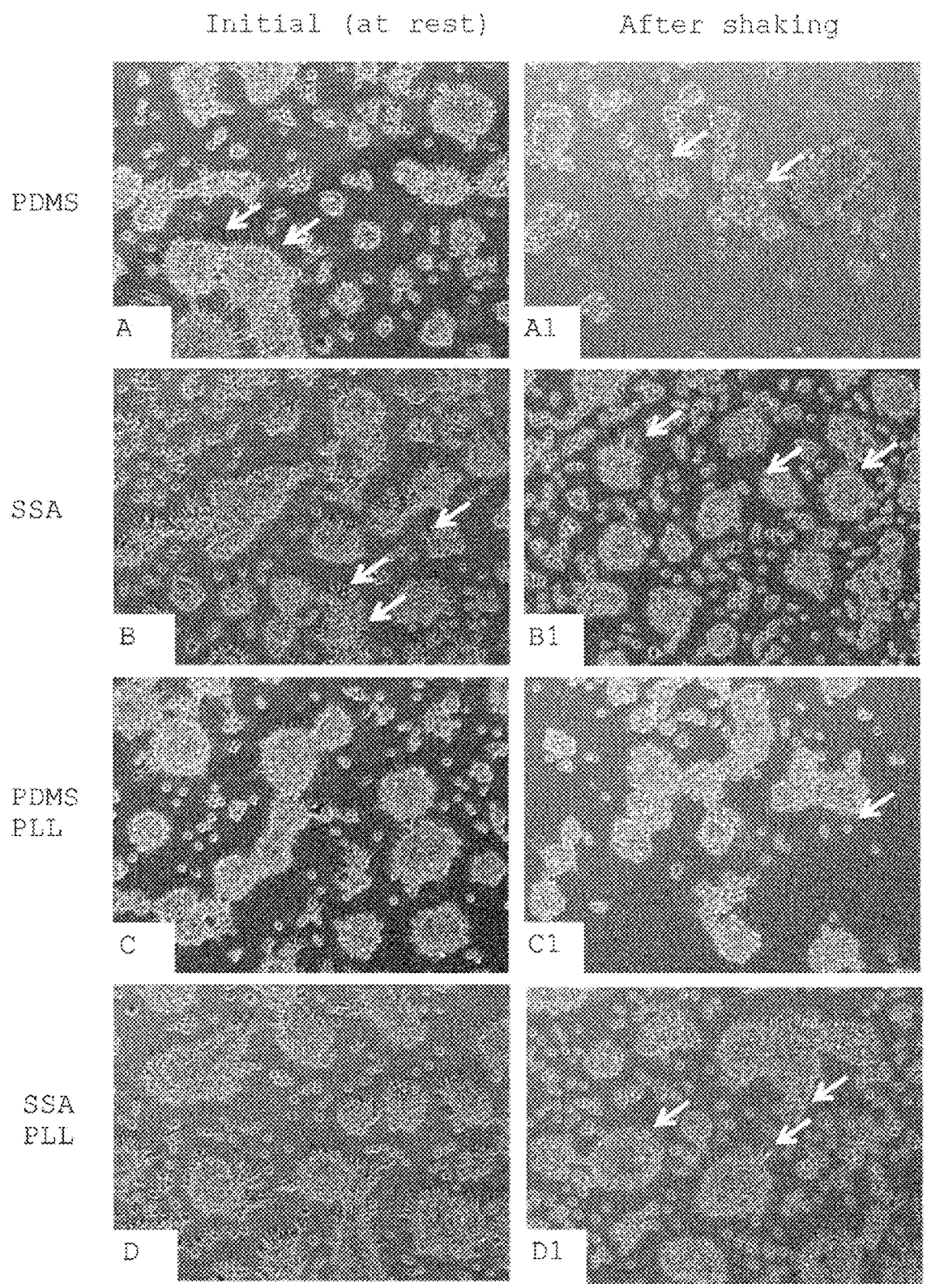
FIG. 14 Micrographs of L929 cells after 48 h on PDMS (A), SSA 50:50 (B), PDMS with PLL (C), SSA 50:50 with PLL (D); images A1, B1, C1 and D1 show the samples after shaking for 60 s.

The adhesion force of L929 cells on the surfaces was also tested. FIG. 14 shows corresponding light micrographs. L929 cells were plated for 48 h on PDMS (A) and SSA 50:50 (B). The average layer thickness was between 130 μm and 200 μm and was determined using an optical system.

In addition, the surface of the polymers was functionalized by applying 0.01% poly-L-lysine (PLL) (PDMS (C) and SSA 50:50 (D)). The cells were plated as individual cells. Generally speaking, one cannot observe any difference microscopically in quantitative cell adhesion between PDMS and SSA, as the cells form extensions on both materials (arrows on the images). On SSA, the cells generally appear to be flatter and more elongated. The same impression can be seen on the PLL coated surfaces (C, D). In order to investigate how the cells behave under mechanical stress, all of the samples were shaken with the same force for a period of approximately 60 s. This leads to significant detachment of the cells from the PDMS surface (A1). The aggregates in this image are no longer in contact with the polymer surface (arrows in in A1). In comparison to this, on the SSA surface one finds a sharp reduction in the cellular extensions compared to A, but no detachment of the surface occurs (B1). The functionalization by means of PLL clearly prevents detachment of the cells on the PDMS surface (C1) and prevents the reduction of the cell extensions on SSA (D1). Nevertheless, the cells appear to be more "spherical" than in FIG. D. This morphology appears to be typical for cells with low adhesion contacts to the surface. In summary, one can say here that the cells on the SSA surface are less sensitive to mechanical stress. Cellular adhesion can be significantly improved by a surface modification, as shown in D1.

SSA 50:50-PDMS composite structures were produced and applied to the intact eardrum of a dead mouse. The composite structure was cut to the required dimensions and then applied with the adhering side to the intact eardrum. Repeated detachment and repositioning did not cause the eardrum to rupture. In a further step, a part of the eardrum was cut open in order to simulate a rupture. It was possible to fasten the composite structure to the edges of the wound and exert a lateral pull.

Figure 16:
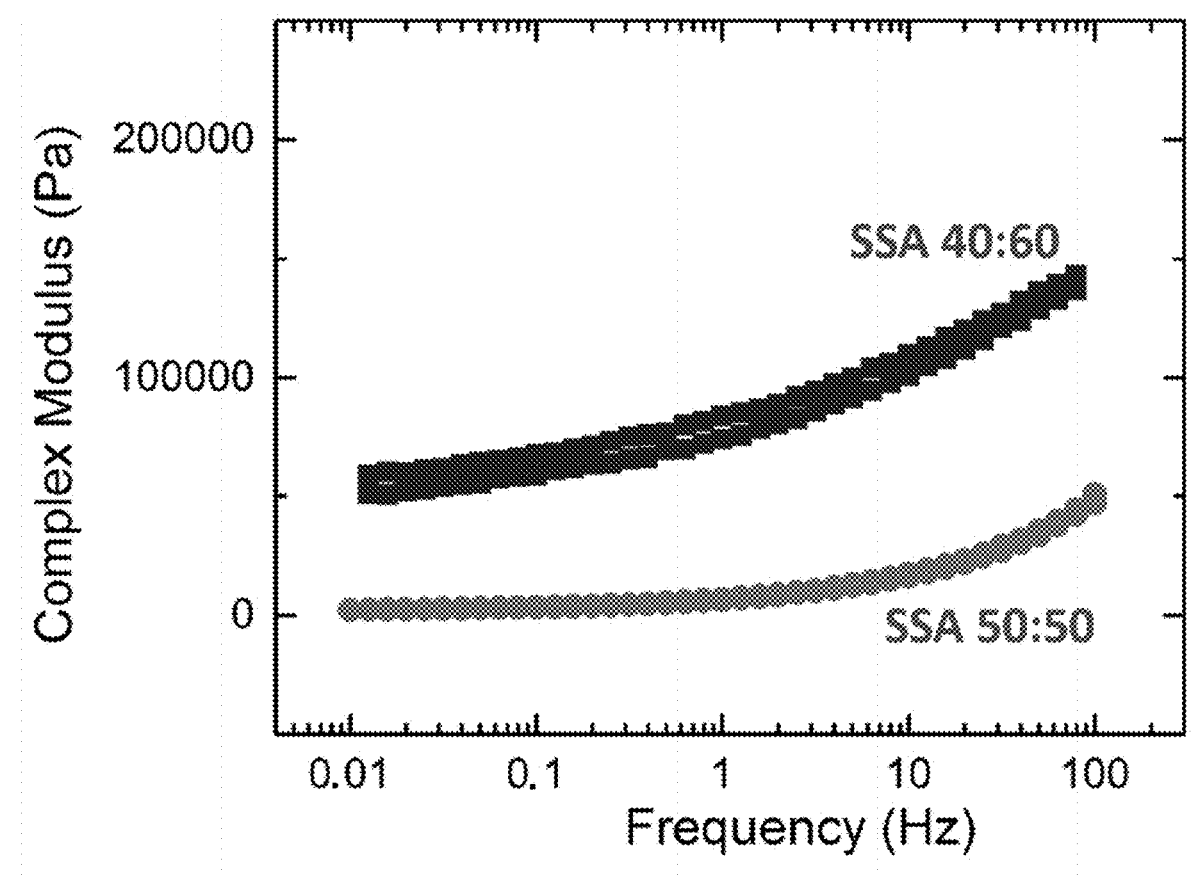
FIG. 16 The complex modulus of SSA 40:60 and SSA 50:50 was determined by rheometry at frequencies of between 0.1 and 100 Hz. The measurement amplitude was 0.1%.

The complex modulus of SSA 40:60 and SSA 50:50 was determined by rheometry at frequencies of between 0.1 and 100 Hz (FIG. 16). The measurement amplitude was 0.1%. The results show that SSA 50:50 has a lower E modulus than SSA 40:60. The approximate ratios were a ratio of about 6 between PDMS 10:1 and SSA 40:60 and a ratio of about 65 between PDMS 10:1 and SSA 50:50.

Figure 17:
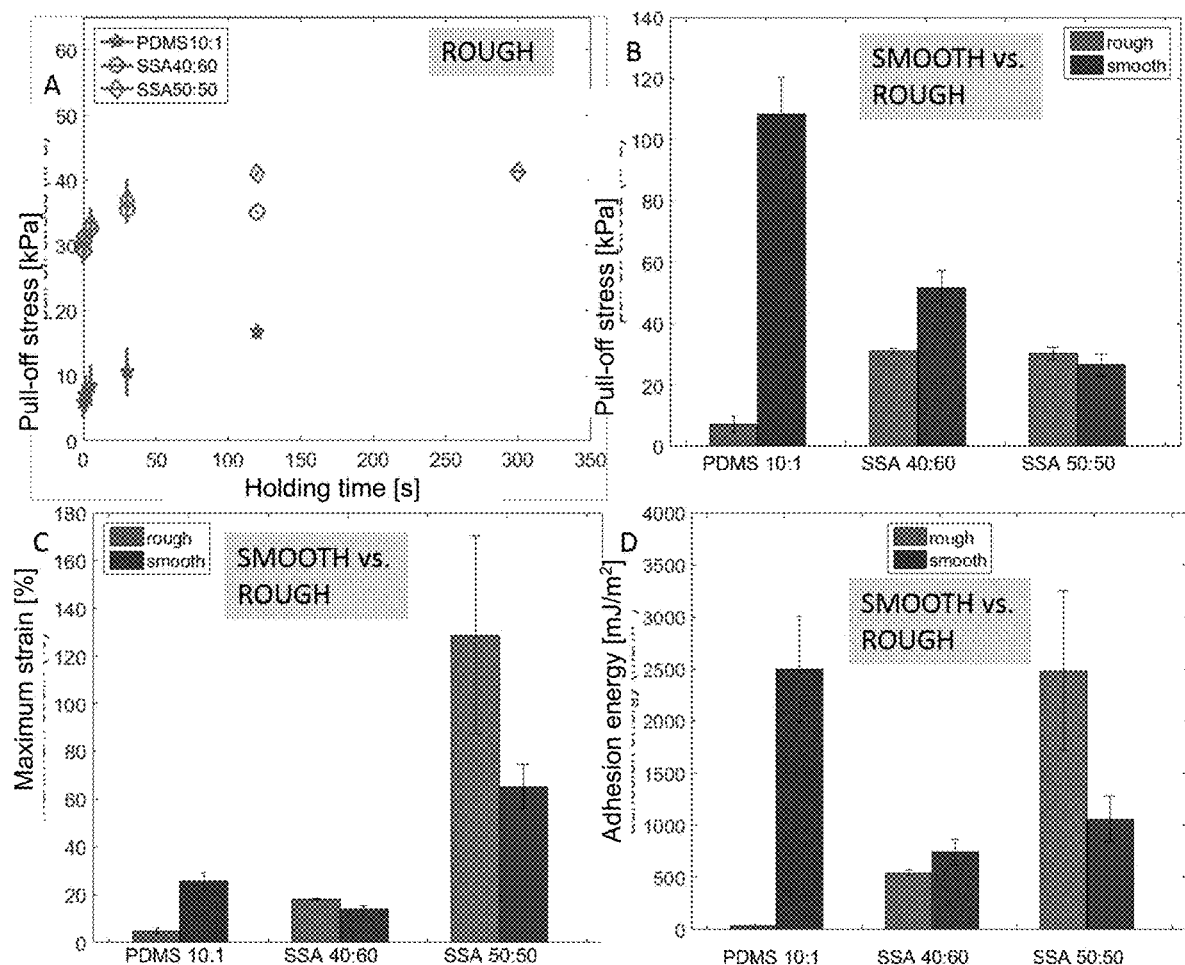
FIG. 17 Comparison of various adhesion parameters between rough substrate and smooth substrate: (A) determination of pull-off stress depending on holding time after the substrate was pressed onto the preparations with a force of approximately 40 mN. The thickness of the preparations, which was tested using rough substrate, was between 130 µm and 170 µm. (B) Comparison of pull-off stress in use of a rough substrate and a smooth substrate. (C) Determination of the maximum strain using a rough substrate and a smooth substrate. (D) Determination of adhesion energy in use of a rough substrate and a smooth substrate.

A comparison of the two substrates to each other shows that the pull-off stress of SSA in use of a rough substrate (glass $R_a$=0.271 μm) is higher than for PDMS (FIG. 17). SSA 50:50 shows comparable pull-off stresses when a rough or smooth substrate ($R_a$=0.006 μm) is used (A, B). The maximum strain of SSA 50:50 is substantially higher for SSA 50:50 than for PDMS (C). The adhesion energy of PDMS is substantially lower in use of a rough substrate than the adhesion energy of SSA 40:60 and SSA 50:50 (D).

This shows that the structured coatings according to the invention are better suited for rough surfaces, i.e. surfaces having a roughness of greater than 0.2 μm. For a mouse eardrum, a roughness of approximately $R_a$=1 μm was measured after vapor deposition of a thin gold film.

FIG. 18 A shows a schematic view of the measuring apparatus for determination of the measurement values. The structured coating (polymer film) is pressed against a substrate (glass substrate) using a moveable (pivotable) table. Both the pressing force and the adhesion force on the substrate when the structured coating is moved away can be measured using a load cell. B shows measurement of the roughness of the glass substrate used for the measurements (roughness measured in all cases by white light interferometry).

FIG. 19 shows the production process. In (1), a structured surface is first produced, which in (2) is then further processed into a structured coating with a further layer. From left to right, (1) shows the application of the first polymer (prepolymer 1) either to a glass slide or a microstructured MD40 master (hexagonally arranged pillar-shaped protrusions with a diameter of 7 µm, a height of 18 µm, and a center-to-center distance of 14 µm) located on a glass slide. New PDMS is applied to the MD40 master, air is withdrawn in a vacuum, and a plasma-activated glass slide is applied to the surface. Weights are applied to this (e.g. 10 g/cm$^2$), which makes it possible to influence the thickness of the PDMS layer, which constitutes the carrier layer for the protrusions (e.g. 40±9 µm). After polymerization at 95° C. to 100° C. for one hour, the MD40 mold can be removed. (2) The second polymer (prepolymer 2, e.g. SSA) can now be applied by the spin-coating method to the microstructured PDMS layer, which is also treated with plasma. The composite structure produced in this manner is polymerized at 95° C. to 100° C. After this, the surface can also be functionalized for biological applications. This method was used to produce both structured coatings and unstructured coatings as comparison samples. The parameter t denotes the thickness of the further layer above the protrusions, while b denotes the thickness of the carrier layer.

Figure 20:
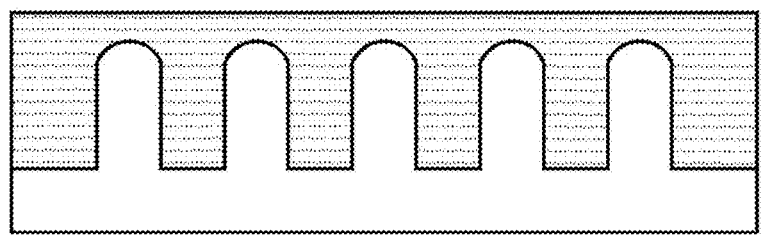
FIG. 20 Schematic view of sections of further embodiments of the invention.
Figure 20:
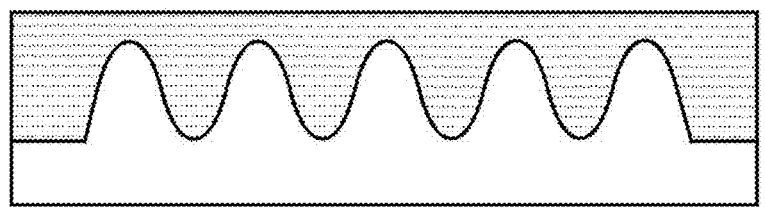

FIG. 20 shows a section of further embodiments of the invention. The protrusions need not have a rectangular shape in a longitudinal section. It is also possible for the end faces of the protrusions to be curved, in particular convex with respect to the further layer (FIG. 20, top).

A further embodiment of the invention is shown at bottom in FIG. 20. Here, the interface between the protrusions and further layer is a wavy line. The protrusions therefore have the three-dimensional form of a paraboloid of revolution.

It is important for all of the variants that there be a sufficiently large area of the further layer in which the perpendicular thickness of the further layer is in accordance with the ratio according to the invention with respect to the height of the protrusions in said area. In these areas with a thinner further layer, advantageous adhesion properties are formed. By avoiding edges in the shape of the protrusions, in particular at their end faces, one can avoid stress peaks on detachment of the device from a surface, which improves adhesion.

REFERENCE NUMBERS

100 Carrier layer
110 Protrusion
120 Further layer
130 Filled intermediate space
140 End face
150 Surface facing the surface of substrate

The invention claimed is:

1. A method for treating eardrum perforations, comprising:
   providing a device comprising
      a carrier layer having a plurality of protrusions comprising an elastomer, each protrusion comprising at least a shaft having an end face pointing away from a surface of the carrier layer, and
      a further layer arranged at least on the end face, wherein this further layer has a different elastic modulus than the respective protrusion; and
   applying the device to a surface of an eardrum having a perforation.

2. The method as claimed in claim 1 wherein the further layer arranged on the end face has a lower elastic modulus than the respective protrusion.

3. The method as claimed in claim 1, wherein the protrusions have an aspect ratio of greater than 1.

4. The method as claimed in claim 1, wherein the protrusions have an aspect ratio of at least 3.

5. The method as claimed in claim 1, wherein the further layer additionally fills the intermediate spaces between the protrusions.

6. The method as claimed in claim 1, wherein the further layer is part of a film that connects the protrusions.

7. The method as claimed in claim 1, wherein the protrusions comprise epoxy- and/or silicone-based elastomers, polyurethane(meth)acrylates, polyurethanes, silicones, silicone resins or polyurethane(meth)acrylates.

8. The method as claimed in claim 1, wherein the further layer comprises a vinyl-terminated silicone.

9. The method as claimed in claim 1, wherein a ratio of elastic moduli between the lowest elastic modulus and an area with the highest elastic modulus is less than 1:2000.

10. The method as claimed in claim 1, wherein a ratio of elastic moduli between the lowest elastic modulus and an area with the highest elastic modulus is less than 1:1200.

11. The method as claimed in claim 1 wherein the device is transparent.

12. The method according to claim 1, wherein no liquid is required for applying the device.

13. A method for treating eardrum perforations, comprising:
   providing a device comprising
      a carrier layer having a plurality of protrusions, each protrusion comprising a shaft having an end face pointing away from a surface of the carrier layer, and
      further layers, each further layer directly contacting the end face of a protrusion and having a lower elastic modulus than that of the respective protrusion, the further layers forming a top surface of the device, wherein the device is a dry adhesive; and
   applying the device to a surface of an eardrum having a perforation.

* * * * *

UNITED STATES PATENT AND TRADEMARK OFFICE
CERTIFICATE OF CORRECTION

PATENT NO. : 11,096,771 B2  
APPLICATION NO. : 16/317048  
DATED : August 24, 2021  
INVENTOR(S) : Arzt et al.

Page 1 of 1

It is certified that error appears in the above-identified patent and that said Letters Patent is hereby corrected as shown below:

On the Title Page

Item (73), Assignee:  
Change "Leibniz-Institut für Neue Materiallen gemeinnützige GmbH, Saarbrücken (DE)"  
To:  
--Leibniz-Institut für Neue Materialien gemeinnützige GmbH, Saarbrücken (DE)--

Signed and Sealed this  
Fifth Day of October, 2021

Drew Hirshfeld  
*Performing the Functions and Duties of the*  
*Under Secretary of Commerce for Intellectual Property and*  
*Director of the United States Patent and Trademark Office*